US00PP08269P

United States Patent [19]

Bradford et al.

[11] Patent Number: Plant 8,269

[45] Date of Patent: Jun. 22, 1993

[54] ALMOND TREE (MORLEY)

[76] Inventors: Lowell G. Bradford, 12439 E. Savana Rd.; Norman G. Bradford, 11875 E. Savana Rd., both of Le Grand, Calif. 95333

[21] Appl. No.: 840,140

[22] Filed: Feb. 24, 1992

[51] Int. Cl.[5] ..... A01H 5/00

[52] U.S. Cl. ..... Plt./32.2

[58] Field of Search ..... Plt./32.2

*Primary Examiner*—James R. Feyrer

[57] ABSTRACT

The present invention relates to an almond tree and more particularly to a new and distinct variety broadly characterized by a large size, vigorous, upright, hardy, very late blooming, very productive, and regular bearing tree whose nuts mature under the ecological conditions described approximately the second week in September. The nuts are very well sealed to protect kernels that are uniformly medium in size, dark in color, and ovate in shape.

1 Drawing Sheet

BACKGROUND OF THE VARIETY

In a continuing effort to improve the quality of shipping fruits and nuts, we, the inventors, typically hybridize a large number of nectarine, peach, plum, apricot, cherry, and almond seedlings each year. The present invention relates to a new and distinct variety of almond tree, which has been denominated varietally as "Morley". The present variety was selected in 1982 by us in a cultivated area of our experimental orchard at Bradford Farms near Le Grand, Calif. in Merced County (San Joaquin Valley). This hybrid seedling resulted from using Texas Almond (unpatented) as the selected seed parent and an unnamed late blooming almond seedling as the selected pollen parent. Subsequent to origination of the present variety of almond tree, we asexually reproduced it by budding and grafting, and such reproduction of plant and nut characteristics were true to the original plant in all respects.

The tree of the present variety is most similar to that of its seed parent, the Texas (unpatented), by being vigorous and upright, but is distinguished therefrom by blooming one week later and by being a more consistent and heavier producer. The nuts produced by the present variety are also similar to those of the Texas variety by having kernels that are medium in size and dark in color, but are distinguished therefrom by being much less susceptible to doubling, by maturing two weeks earlier and by having shells that are more easily removed from the kernels by mechanical shelling processes with very little scratching and breaking.

The present variety differs significantly from the well known Nonpareil Almond (unpatented) variety in several ways, but most distinctively by blooming and harvesting approximately two weeks later.

DRAWING

The accompanying color photograph exhibits nuts in hull, exposed hulls, nuts out of hull, kernels out of shell, and leaves, all typical of the instant variety.

POMOLOGICAL CHARACTERISTICS

Referring now more specifically to the pomological characteristics of this new and distinct variety of almond tree, the following has been observed under the ecological conditions prevailing near Le Grand, Merced County (San Joaquin Valley), Calif., and was developed at the harvest stage on Sep. 15, 1991. All major color code designations are by reference to the Inter-Society Color Council, National Bureau of Standards. Common color names are also used occasionally.

TREE

Size: Large.
Vigor: Vigorous.
Growth: Upright and dense.
Form: Vase formed.
Hardiness: Hardy.
Production: Very productive.
Bearing: Regular bearer.
Trunk:
- *Size.*—Medium.
- *Texture.*—Shaggy.
- *Bark color.*—Dark grayish brown [62. d.gy.Br].
- *Lenticels.*—Numerous. Color: Grayish yellowish brown [80. gy.yBr]. Average Size: ⅜" [9.5 mm.].

Branches:
- *Size.*—Medium.
- *Texture.*—Smooth.
- *Color.*—1st Year wood: Moderate yellow green [120. m.YG]. Older wood: Grayish yellowish brown [80. gy.yBr].
- *Lenticels.*—Numerous, very small.

Leaves:
- *Size.*—Medium. Average length: 4⅜" [111.1 mm.]. Average width: 15/16" [33.3 mm.].
- *Thickness.*—Medium.
- *Form.*—Elliptical.
- *Apex.*—Acuminate.
- *Base.*—Acute.
- *Surface.*—Smooth.
- *Color.*—Dorsal surface: Dark olive green [126. d.OlG]. Ventral surface: Moderate olive green [125. m.OlG].
- *Margin.*—Serrate.
- *Venation.*—Pinnately net veined.
- *Petiole.*—Average length: 1" [25.4 mm.]. Average thickness: 1/16" [1.6 mm.]. Dorsal color: Moderate olive green [125. m.OlG]. Ventral color: Moderate yellow green [120. m.YG].
- *Stipules.*—Few. Average Length: 3/16" [4.8 mm.].
- *Glands.*—Average Number: Mostly 4 to 6 per leaf. Position: Mostly oppositely positioned on petiole and base of blade. Size: Small. Form: Globose. Color: Strong yellow green [117. s.YG].

Flower buds:

*Hardiness.*—Hardy.

*Size.*—Medium.

*Length.*—Medium.

*Form.*—Free.

*Surface.*—Pubescent.

Flowers:

*Blooming period.*—Approximately 2 weeks later than Nonpareil, 1 week later than Texas.

*Blooming duration.*—Medium.

*Type.*—Self-sterile, must be cross pollinated by other later blooming varieties.

*Amount of Bloom.*—Heavy.

*Size.*—Large.

*Color.*—White [263. White].

HULL

Outer surface: Smooth, Pubescent.

Form: Uniform, symmetrical.

*Longitudinal section form.*—Oval.

Average thickness: 1/16" [1.6 mm] when dry.

Flesh: Tough, but brittle when dry.

Suture: A sharp crack prior to splitting.

External color: Grayish greenish yellow [105. gy.gY].

Dehiscence: Opens freely.

Splitting: Complete along suture.

Adherence: Hulls are easily removed from nuts by mechanical hullers.

Density: Hulls are relatively light.

Nut cavity: Oval.

*Surface.*—Rough.

*Color when first opened.*—Light orange yellow [70. l.OY].

*Color when dry.*—Dark orange yellow [72. d.OY].

NUT

Size:

*Average length.*—1 3/16" [30.2 mm.].

*Average width.*—$\frac{3}{4}$" [19.1 mm.].

*Average thickness.*—$\frac{1}{2}$" [12.7 mm.].

*Average weight.*—13.4 nuts per ounce [2.1 grams per nut].

Form: Ovate.

Shell:

*Color.*—Light yellowish brown [76. l.yBr].

*Average wall thickness.*—1/16" [1.6 mm.].

*Pits.*—Small, numerous.

*Outer shell.*—Crumbling.

*Inner shell.*—Thin, brittle, well sealed.

Base: Slightly oblique.

Apex: Acute.

Stem: Medium.

*Average length.*—$\frac{1}{4}$" [6.4 mm.].

*Average diameter.*—3/16" [4.8 mm.].

Wing: Thin, shorter near base.

*Average protrusion.*—1/16" [1.6 mm.].

Inner surface: Smooth.

*Color.*—Light yellowish brown [76. l.yBr].

KERNEL

Size: Medium to large.

*Average length.*—$\frac{7}{8}$" 22.2 mm.].

*Average width.*—17/32" [13.5 mm.].

*Average thickness.*—11/32" [8.7 mm.].

*Average weight.*—23.8 nuts per ounce [1.2 grams per nut].

Form: Uniform, symmetrical.

*Longitudinal section form.*—Ovate.

*Transverse section form.*—Elliptical.

Base: Slightly oblique, shouldered on one side, rounded on the other.

Apex: Acute.

Surface: Slightly wrinkled.

*Pellicle color.*—Strong yellowish brown [74. s.yBr].

*Veins.*—Deep yellowish brown [75. deep yBr] veins extending longitudinally from the base to the apex with some branching.

Doubling: Rarely observed.

Number of defective kernels: Very few on most years.

Flavor: Good typical almond flavor.

Astringency: Very slight.

Quality: Very good.

Viable: Yes.

Blanchable: Yes.

Percentage of kernel to nut: b 56.4%.

CULTURAL CHARACTERISTICS

Resistance to insects: Resistant to kernel insect damage due to its very well sealed inner shell.

Susceptibility to budfailure: No obvious occurrences of budfailure have been observed as of yet.

Resistance to other diseases: No unusual susceptibilities noted.

Susceptibility to frost: No unusual susceptibility noted, but the exposure duration is shorter than most varieties due to the late onset of blooming.

Although the new variety of almond tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of almond tree, substantially as illustrated and described, which is most similar to its seed parent, the Texas (unpatented), by being vigorous and upright in growth and by producing dark medium sized kernels that are protected from insects by a well sealed shell, but is distinguished therefrom and an improvement thereon by appearing to be a heavier and more consistent producer, by blooming one week later while harvesting two weeks earlier, and by producing nuts that are much less prone to doubling and much easier to shell without causing mechanically induced damage to the kernel.

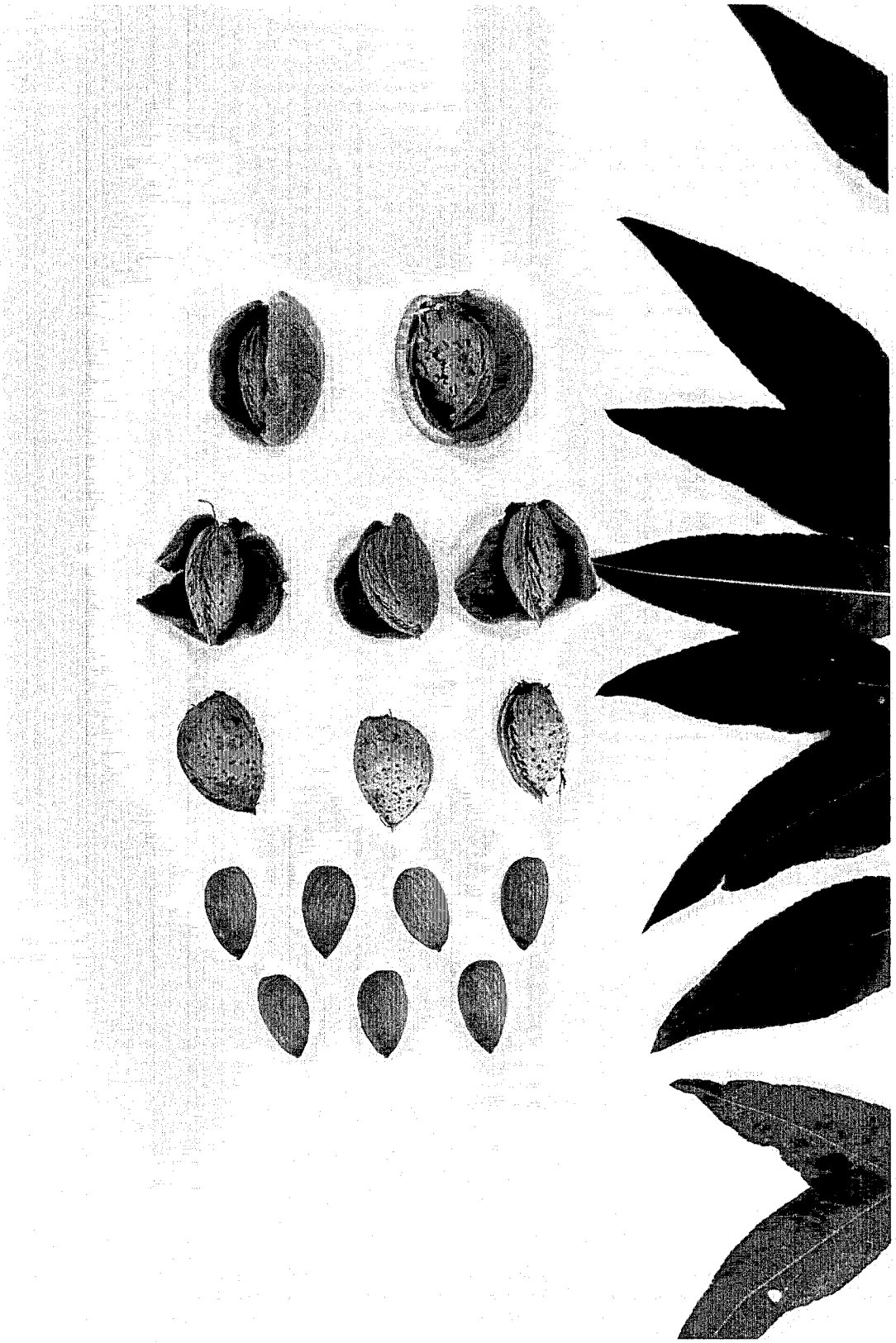

* * * * *